United States Patent
Safo et al.

(10) Patent No.: US 10,344,001 B2
(45) Date of Patent: Jul. 9, 2019

(54) AZOLYLACRYLOYL DERIVATIVES AS THERAPEUTIC AGENTS FOR SICKLE CELL DISEASE

(71) Applicant: VIRGINIA COMMONWEALTH UNIVERSITY, Richmond, VA (US)

(72) Inventors: Martin K. Safo, Richmond, VA (US); Yan Zhang, Glen Allen, VA (US); Mohini Ghatge, Glen Allen, VA (US); Osheiza Abdulmalik, Philadelphia, PA (US); Abdelsattar Mansour Ebid Omar, Jeddah (SA); Moustafa El-Sayed El-Araby, Jeddah (SA)

(73) Assignees: VIRGINIA COMMONWEALTH UNIVERSITY, Richmond, VA (US); KING ABDULAZIZ UNIVERSITY, Jeddah (SA); THE CHILDREN'S HOSPITAL OF PHILADELPHIA, Philadelphia, PA (US)

( * ) Notice: Subject to any disclaimer, the term of this patent is extended or adjusted under 35 U.S.C. 154(b) by 0 days.

(21) Appl. No.: 15/764,052

(22) PCT Filed: Sep. 30, 2016

(86) PCT No.: PCT/US2016/054684
§ 371 (c)(1),
(2) Date: Mar. 28, 2018

(87) PCT Pub. No.: WO2017/059204
PCT Pub. Date: Apr. 6, 2017

(65) Prior Publication Data
US 2018/0282287 A1    Oct. 4, 2018

Related U.S. Application Data

(60) Provisional application No. 62/236,486, filed on Oct. 2, 2015.

(51) Int. Cl.
| | | |
|---|---|---|
| *A61K 31/4174* | (2006.01) |
| *A61K 31/4178* | (2006.01) |
| *C07D 233/58* | (2006.01) |
| *A61P 7/00* | (2006.01) |
| *C07D 405/12* | (2006.01) |
| *C07D 233/64* | (2006.01) |

(52) U.S. Cl.
CPC ........ *C07D 233/58* (2013.01); *A61K 31/4174* (2013.01); *A61K 31/4178* (2013.01); *A61P 7/00* (2018.01); *C07D 233/64* (2013.01); *C07D 405/12* (2013.01)

(58) Field of Classification Search
CPC .................... A61K 31/4174; A61K 31/4178
See application file for complete search history.

(56) References Cited

U.S. PATENT DOCUMENTS

| | | |
|---|---|---|
| 4,699,926 A | 10/1987 | Abraham et al. |
| 5,273,992 A | 12/1993 | Brugnara et al. |
| 6,071,943 A | 6/2000 | Shiori et al. |
| 2006/0014781 A1 | 1/2006 | Wagle et al. |
| 2006/0257852 A1 | 11/2006 | Rappuoli et al. |

OTHER PUBLICATIONS

Chemical Abstracts Registry No. 228571-15-1, indexed in the Registry file on STN CAS Online on Jul. 22, 1999. (Year: 1999).*
Solomon et al., Biomedicine & Pharmacotherapy, 66, 2012, pp. 213-220 (Year: 2012).*

* cited by examiner

*Primary Examiner* — Laura L Stockton
(74) *Attorney, Agent, or Firm* — W&C IP (57) ABSTRACT

Azolylacryloyl derivatives with hypoxic properties are provided. The compounds have a generic formula: and are suitable for treating sickle cell disease and hypoxia-underlying diseases, e.g. hemorrhagic and traumatic shock, cardiac arrest and cardiogenic shock, traumatic brain injury, cancer, stroke, myocardial infarction, myocardial ischemia, vaso-occlusive crisis, etc.

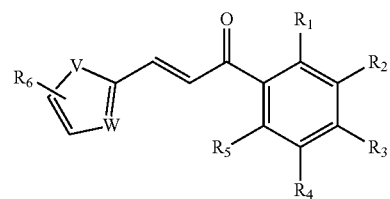

2 Claims, 5 Drawing Sheets

AZOLYLACRYLOYL DERIVATIVES AS THERAPEUTIC AGENTS FOR SICKLE CELL DISEASE

CROSS-REFERENCE TO RELATED APPLICATIONS

This application claims benefit of U.S. provisional patent application 62/236,436, filed Oct. 2, 2015, the complete contents of which is hereby incorporated by reference.

STATEMENT OF FEDERALLY SPONSORED RESEARCH AND DEVELOPMENT

This invention was made with government support under Grant MD009124 awarded by the National Institutes of Health/National Institute on Minority Health and Health Disparities and Grant K01HL102186 awarded by the National Institutes of Health/National Heart, Lung and Blood Institute. The United States government has certain rights in the invention.

BACKGROUND OF THE INVENTION

Field of the Invention

The invention generally relates to agents with hypoxic properties for treating disease. In particular, the invention provides azolylacryloyl derivatives with hypoxic properties that are suitable for treating sickle cell disease, and hypoxia-underlying diseases, including but not limited to hemorrhagic and traumatic shock, cardiac arrest and cardiogenic shock, traumatic brain injury, cancer, stroke, myocardial infarction, myocardial ischemia, and vaso-occlusive crisis.

Background

Sickle hemoglobin (HbS) when deoxygenated or under hypoxic condition polymerizes into rigid and insoluble fibres that cause the primary pathophysiology associated with sickle cell disease (SCD) leading to several secondary pathological effects, including but not limited to adhesion of red blood cells (RBCs) to tissue endothelium, oxidative stress, hemolysis of RBCs, decreased vascular nitric oxide bioavailability, inflammation, vaso-occlusion, impaired microvascular blood flow, painful crises, hemolytic anemia, morbidity and mortality[1-4]. Although various supportive therapies are available, the only disease-modifying drug approved for treatment of adults with SCD is hydroxyurea, originally an anti-cancer drug[5]. However, not all patients respond to hydroxyurea. It can be poorly tolerated and can cause myelosuppression, requires frequent monitoring for life-threatening side effects, and many people in the developing world do not have access to this drug. There has been little progress in the development of other disease-modifying agents since 1995. Therefore, safer, less expensive, easy to administer and more effective therapeutic agents are needed to treat SCD patients, particularly children.

Hemoglobin (Hb) functions in equilibrium between the unliganded or deoxygenated tense (T) state which exhibits low affinity for ligand, and the liganded or oxygenated relaxed (R) state which exhibits high affinity for ligand. Sickle RBCs have significantly reduced affinity for oxygen compared to normal RBCs, presumably as a result of increased intracellular concentration of 2,3-DPG and/or sphingosine phosphate in sickle erythrocytes, leading to premature release of oxygen and increasing RBC sickling[6-9]. This has led to a rational approach to treat the disease by shifting Hb oxygen equilibrium curve (OEC) to the left (i.e. stabilizing the R state and/or destabilizing the T state), producing a high-affinity Hb that more readily binds and holds oxygen, thus preventing hypoxia-induced polymerization and the concomitant erythrocyte sickling[10, 11]. The degree of shift in the OEC is reported as a decrease (left-shift) or increase (right-shift) in $P_{50}$ (oxygen tension at 50% Hb $O_2$ saturation). Several aromatic aldehydes are known to have this allosteric and/or pharmacologic property by forming a Schiff-base covalent interaction in a symmetry-related fashion with the two N-terminal αVal1 nitrogens at the α-cleft of liganded Hb, and through several inter-subunit mediated hydrogen-bond and/or hydrophobic interactions tie the two α-subunits together (cross-link the two α-subunits) to stabilize the R-state Hb[9-17].

However, a problem with aromatic aldehydes is that the allosteric and/or antisickling effect of such compounds, which is due to Schiff-base formation with the N-terminal of the αVal1 nitrogen of Hb, is transient and not stable. Also, the aldehyde moiety is readily susceptible to metabolic destruction by aldehyde dehydrogenase. Other compounds with antisickling activities, e.g. ethacrynic acid (ECA), are known to bind to βCys93 of Hb through a Michael addition reaction and disulfide bond formation, respectively, thereby destabilizing the T-state and resulting in increased Hb oxygen affinity[18, 19]. However, the diuretic activity of ECA precludes its use as an oral therapeutic agent for the treatment of SCD.

There is a pressing need to provide safer, less expensive, easily administered and more effective therapeutic agents to treat SCD patients, particularly children. In particular, there is a need to provide agents that do not suffer from the drawbacks associated with known SCD agents.

SUMMARY OF THE INVENTION

Other features and advantages of the present invention will be set forth in the description of invention that follows, and in part will be apparent from the description or may be learned by practice of the invention. The invention will be realized and attained by the compositions and methods particularly pointed out in the written description and claims hereof.

The present invention provides novel azolylacryloyl derivatives that form covalent interactions with Hb and increase the protein's affinity for oxygen, with a concomitant antisickling effect. These compounds bind covalently with Hb through a Michael addition reaction with the βCys93, as well as potentially bind with the free N-terminal αVal1 amine at the α-cleft of the protein, thereby stabilizing the relaxed state Hb, increasing the protein's affinity for oxygen and preventing hypoxia-related polymerization. Additionally, the compounds have several secondary pharmacologic effects, including prevention of oxidative stress, hemolysis, inflammation, and increasing oxygenation of hypoxic tissues. The covalent binding nature, and the multiple therapeutic effects of these compounds also advantageously decrease the therapeutic dose required for efficacy, compared to known SCD drugs. In addition, the compounds are not readily susceptible to metabolic destruction and thus have an extended therapeutic duration of action.

The compounds have a generic formula:

FORMULA I where V and W are the same or different and are independently C, O, S, N or NH. Substitution if present could be halogen, amine, alkyl, ester, ether, or other moieties;
and where R1, R2, R3, R4, R5 and R6 are the same or different and are independently any of i) H, OH, or halogen, ii) substituted or unsubstituted alkyl, alkoxy, hydroxyl-alkyl, halogen, aryl or O-aryl; or iii) M, where M is and where R7 and R8 are the same or different and are independently H, OH, alkyl, alkoxy, hydroxyl-alkyl, halogen, aryl or O-aryl;
X, Y and Z are independently C (forming part of the phenyl ring) or N (forming a substituted phenyl), and may be the same or different; and
B is a bridging or linking chain that connects M to the phenyl moiety of Formula I (the asterisk (*) marks the point of attachment of M to the phenyl moiety of Formula 1). The backbone of bridging chain B is generally from about 2 to about 8 atoms in length, and the bonds between the atoms of the backbone may be saturated or unsaturated. The atoms and/or atomic groups that make up B include but are not limited to: CH$_2$, CO, O, S, NH, NHCO, NHCONH, and OCO. Substitutions, if present, could be halogen, amine, sulfyl, alkyl, ester, ether, or other moieties.

These new compounds with antisickling properties are useful for the treatment of diseases that can be ameliorated by increasing Hb oxygen affinity, for example, sickle cell disease, and hypoxia-underlying or associated diseases, e.g. hemorrhagic and traumatic shock, cardiac arrest and cardiogenic shock, traumatic brain injury, cancer, stroke, myocardial infarction, myocardial ischemia, vaso-occlusive crisis, etc.

It is an object of this invention to provide compounds of Formula I

FORMULA I where V and W are the same or different and are independently C, O, S, N or NH;

and where R1, R2, R3, R4, R5 and R6 are the same or different and are independently any of i) H, OH, or halogen, ii) substituted or unsubstituted alkyl, alkoxy, hydroxyl-alkyl, halogen, aryl or O-aryl; or iii) M, where M is where
R7 and R8 are the same or different and are independently H, OH, alkyl, alkoxy, hydroxyl-alkyl, halogen, aryl or O-aryl;
X, Y and Z may be the same or different and are independently C or N; and
B is a bridging moiety that connects M to the phenyl moiety of Formula I.

In some aspects, a backbone of bridging moiety B is from about 2 to about 8 atoms in length. In further aspects, one or more substituents of B are selected from the group consisting of: CH$_2$, CO, O, S, NH, NHCO, NHCONH, and OCO. In yet further aspects, B is —CH$_2$O—.

In further aspects, the compound of Formula 1, is

The invention also provides methods of treating sickle cell disease in a subject in need thereof. The methods comprise administering to the subject a therapeutically effective amount of a compound of Formula I Formula I where V and W are the same or different and are independently C, O, S, N or NH; and where R1, R2, R3, R4, R5 and R6 are the same or different and are independently any of i) H, OH, or halogen, ii) substituted or unsubstituted alkyl, alkoxy, hydroxyl-alkyl, halogen, aryl or O-aryl; or iii) M, where M is where

R7 and R8 are the same or different and are independently H, OH, alkyl, alkoxy, hydroxyl-alkyl, halogen, aryl or O-aryl;

X, Y and Z may be the same or different and are independently C or N; and

B is a bridging moiety that connects M to the phenyl moiety of Formula I.

In further aspects, the invention provides methods of treating a hypoxia-associated disease or condition in a subject in need thereof, comprising administering to the subject a therapeutically effective amount of a compound of Formula I

FORMULA I where V and W are the same or different and are independently C, O, S, N or NH;

and where R1, R2, R3, R4, R5 and R6 are the same or different and are independently any of i) H, OH, or halogen, ii) substituted or unsubstituted alkyl, alkoxy, hydroxyl-alkyl, halogen, aryl or O-aryl; or iii) M, where M is where R7 and R8 are the same or different and are independently H, OH, alkyl, alkoxy, hydroxyl-alkyl, halogen, aryl or O-aryl;

X, Y and Z may be the same or different and are independently C or N; and

B is a bridging moiety that connects M to the phenyl moiety of Formula I.

In some aspects, the hypoxia-associated disease or condition is, for example, hemorrhagic shock, traumatic shock, cardiac arrest, cardiogenic shock, traumatic brain injury, cancer, stroke, myocardial infarction, myocardial ischemia, or vaso-occlusive crisis.

DETAILED DESCRIPTION

Provided herein are novel OEC left-shifting (high-$O_2$-affinity) antisickling agents that are not readily susceptible to metabolic destruction, and are able to form stable covalent interactions with Hb via a Michael addition reaction with the protein.

Exemplary features of the invention include at least the following:

a. The azolylacryloyl derivatives are novel because they form a Michael addition reaction that involves the β-unsaturated carbon and the surface-located βCys93 sulfur and possibly with the α-cleft αVal1 nitrogens of Hb to prevent Hb S polymerization. This potential dual effect is different from aromatic aldehydes that form a Schiff-base reaction between the aldehyde and the αVal1 nitrogens of Hb to prevent Hb S polymerization.

b. Previous azolylacryloyl-based agents, e.g. KAUS-15 also underwent Michael addition reactions with Hb[20]. However, the compounds showed minimal allosteric and/or antisickling activity due to the presence of carboxylate structural moiety which allowed stabilization of the T-state relative to the R-state[20]. The present azolylacryloyl derivatives have no carboxylate and are able to preferentially stabilize the R-state more than the T-state with a concomitant increase in Hb affinity for oxygen and antisickling activity c. The allosteric and/or antisickling effect of previously known aromatic aldehydes is due to Schiff-base formation with the N-terminal αVal1 nitrogens of Hb[9-17]. This reaction is transient and thus not stable. In contrast, the Michael addition reaction formed by the present azolylacryloyl derivatives is a stable covalent interaction. Thus the present azolylacryloyl derivatives exhibit a longer duration of action than previously known aromatic aldehydes.

d. The active aldehyde moiety of the previously known aromatic aldehydes is very susceptible to metabolism by aldehyde dehydrogenase. Thus, these agents suffer from low oral bioavailability, and a large amount of the drug must be used for therapy. In contrast, the active β-unsaturated carbon of the present azolylacryloyl derivatives is metabolically very stable, conferring high oral bioavailability, and permitting the use of smaller doses to achieve an anti-sickling effect.

e. The present compounds are highly selective for binding to the hemoglobin α-cleft and/or βCys93.

In addition to increasing the oxygen affinity of Hb to prevent polymer formation and erythrocyte sickling, the azolylacryloyl derivatives also directly destabilize HbS polymer formation because they interact with the protein surface-located βCys93 amino acid that prevent close association of HbS molecules The compounds have a generic formula:

FORMULA I

Where V and W are the same or different and are independently C, O, S, N or NH. Substitution if present could be halogen, amine, alkyl, ester, ether, or other moieties; and and where R1, R2, R3, R4, R5 and R6 are the same or different and are independently any of i) H, OH, or halogen, ii) substituted or unsubstituted alkyl, alkoxy, hydroxyl-alkyl, halogen, aryl or O-aryl; iii) or M, where M is and where R7 and R8 are the same or different and are independently H, OH, alkyl, alkoxy, hydroxyl-alkyl, halogen, aryl or O-aryl;

X, Y and Z are independently C (forming part of the phenyl ring) or N (forming a substituted phenyl), and may be the same or different; and B is a bridging or linking chain that connects M to the phenyl moiety of Formula I (the asterisk (*) marks the point of attachment of M to the phenyl moiety of Formula 1). The backbone of bridging chain B is generally from about 2 to about 8 atoms in length, and the bonds between the atoms of the backbone may be saturated or unsaturated. The atoms and/or atomic groups that make up B include but are not limited to: $CH_2$, CO, O, S, NH, NHCO, NHCONH, and OCO. Substitutions, if present, could be halogen, amine, sulfyl, alkyl; ester ether, or other moieties.

Exemplary B equivalents include but are not limited to: —$(CH_2)_n$—, where n=2-8; —$CH_2CO$—, etc.

The term "alkyl," as used herein, is inclusive of both straight chain and branched chain saturated groups from 1 to 20 carbons unless otherwise specified. Alkyl groups include but are not limited to: methyl, ethyl, n- and iso-propyl, n-, sec-, iso- and tert-butyl, neopentyl, and the like, and may be optionally substituted with one, two, three, or, in the case of alkyl groups of two carbons or more, four substituents e.g. alkoxy; alkylsulfinyl; amino, azido, halo, heterocyclyl)oxy, hydroxyl, nitro, oxo, thioalkoxy, thiol, etc.

The term "alkoxy" represents a chemical substituent of formula —OR, where R is a $C_{1-20}$ alkyl group (e.g., $C_{1-6}$ or $C_{1-10}$ alkyl), and wherein R may be a cyclic ring, e.g. substituted or unsubstituted cyclohexane. Exemplary alkoxy groups include but are not limited to: methoxy, ethoxy, propoxy (e.g., n-propoxy and isopropoxy), t-butoxy, and the like. In some embodiments, the alkyl group or cyclic alkyl ring can be further substituted with 1, 2, 3, or 4 substituent groups as defined herein (e.g., 0, hydroxyl, alkoxy, etc).

The term "aryl," as used herein, represents a mono-, bicyclic, or multicyclic carbocyclic ring system having one or two aromatic rings. "Aryl" includes but is not limited to: phenyl, naphthyl, 1,2-dihydronaphthyl, 1,2,3,4-tetrahydronaphthyl, anthracenyl, phenanthrenyl, fluorenyl, indanyl, indenyl, and the like, and may be optionally substituted with 1, 2, 3, 4, or 5 substituents e.g. $C_{1-7}$ acyl, $C_{1-20}$ alkyl, $C_{1-20}$ alkoxy, $C_{1-6}$ alkylsulfinyl, $C_{6-10}$ aryl, amino, $C_{1-6}$ alk-$C_{6-10}$ aryl, azido, $C_{3-8}$ cycloalkyl, $C_{1-6}$ alk-$C_{3-8}$ cycloalkyl, halogen, $C_{1-12}$ heterocyclyl, ($C_{1-12}$ heterocyclyl)oxy, hydroxyl, nitro, thiol; $C_{6-10}$ aryloxy, $C_{3-8}$ cycloalkoxy, $C_{6-10}$ aryl-$C_{1-6}$ alkoxy, $C_{1-6}$ alk-$C_{1-12}$ heterocyclyl, $C_{2-20}$ alkenyl, and $C_{2-20}$ alkynyl. In some embodiments, each of these groups can be further substituted as described herein. For example, the alkylene group of a $C_1$-alkaryl or a $C_1$-alkheterocyclyl can be further substituted with an oxo group to afford the respective aryloyl and (heterocyclyl)oyl substituent group.

The term "halogen," as used herein, represents a halogen including, for example, bromine, chlorine, iodine, or fluorine. Halogens may be directly substituted at positions r1-R6, or may be substituted on alkyls, alkoxy, or other moieties at R1-R6.

The term "hydroxyalkyl," as used herein, represents an alkyl group, as defined herein, substituted by one to three hydroxy groups, with the proviso that no more than one hydroxy group may be attached to a single carbon atom of the alkyl group, and is exemplified by hydroxymethyl, dihydroxypropyl, and the like.

Exemplary azolylacryloyl derivatives include but are not limited to:

Formula II

(also referred to herein as KAUS-28)

Formula III

(also referred to herein as KAUS-29)

Formula IV

(also referred to herein as KAUS-30)

Formula V

(also referred to herein as KAUS-31)

Formula VI

(also referred to herein as KAUS-32)

Formula VII

(also referred to herein as KAUS-33)

Formula VIII

(also referred to herein as KAUS-34)

Formula IX (also referred to herein as KAUS-36)

Formula X

; and (also referred to herein as KAUS-38)

Formula XI (also referred to herein as KAUS-39)

The invention also provides methods for treating a subject having SCD or one or more hypoxia-underlying diseases or conditions, e.g. hemorrhagic and traumatic shock, cardiac arrest and cardiogenic shock, traumatic brain injury, cancer, stroke, myocardial infarction, myocardial ischemia, vaso-occlusive crisis, etc. The methods generally involve administering, to a subject diagnosed with SCD or at least one hypoxia-underlying disease or condition, a therapeutically effective amount of one or more compounds as described herein. The methods may include a step of diagnosing a subject with SCD or hypoxia-underlying diseases, e.g. hemorrhagic and traumatic shock, cardiac arrest and cardiogenic shock, traumatic brain injury, cancer, stroke, myocardial infarction, myocardial ischemia, vaso-occlusive crisis, etc.

A "therapeutically effective amount" is an amount sufficient to alleviate or eliminate signs or symptoms of the disease. In some aspects, from about 1 mg to about 1000 mg of the compound, e.g. from about 1, 5, 10, 20, 30, 40, 50, 60, 70, 80, 90, 100, 150, 200, 250, 300, 350, 400, 450, 500, 550, 600, 650, 700, 750, 800, 850, 900, 950, or 1000 mg of a compound is administered, including all multiples of 5 and 10 between 1 and 1000 (e.g. 100, 105, 110, 115, etc.).

The compounds described herein are generally delivered (administered) as a pharmaceutical composition. Such pharmaceutical compositions generally comprise at least one of the disclosed compounds, i.e. one or more than one (a plurality) of different compounds (e.g. 2 or more such as 2, 3, 4, 5, 6, 7, 8, 9, 10 or more) may be included in a single formulation. Accordingly, the present invention encompasses such formulations/compositions. The compositions generally include one or more substantially purified compounds as described herein, and a pharmacologically suitable (physiologically compatible) carrier, which may be aqueous or oil-based. In some aspects, such compositions are prepared as liquid solutions or suspensions, or as solid forms such as tablets, pills, powders and the like. Solid forms suitable for solution in, or suspension in, liquids prior to administration are also contemplated (e.g. lyophilized forms of the compounds), as are emulsified preparations. In some aspects, the liquid formulations are aqueous or oil-based suspensions or solutions. In some aspects, the active ingredients are mixed with excipients which are pharmaceutically acceptable and compatible with the active ingredients, e.g. pharmaceutically acceptable salts. Suitable excipients include, for example, water, saline, dextrose, glycerol, ethanol and the like, or combinations thereof. In addition, the composition may contain minor amounts of auxiliary substances such as wetting or emulsifying agents, pH buffering agents, preservatives, and the like. If it is desired to administer an oral form of the composition, various thickeners, flavorings, diluents, emulsifiers, dispersing aids or binders and the like are added. The composition of the present invention may contain any such additional ingredients so as to provide the composition in a form suitable for administration. The final amount of compound in the formulations varies, but is generally from about 1-99%. Still other suitable formulations for use in the present invention are found, for example in Remington's Pharmaceutical Sciences, 22nd ed. (2012; eds. Allen, Adejarem Desselle and Felton).

Some examples of materials which can serve as pharmaceutically acceptable carriers include, but are not limited to, ion exchangers, alumina, aluminum stearate, lecithin, serum proteins (such as human serum albumin), buffer substances (such as twin 80, phosphates, glycine, sorbic acid, or potassium sorbate), partial glyceride mixtures of saturated vegetable fatty acids, water, salts or electrolytes (such as protamine sulfate, disodium hydrogen phosphate, potassium hydrogen phosphate, sodium chloride, or zinc salts), colloidal silica, magnesium trisilicate, polyvinyl pyrrolidone, polyacrylates, waxes, polyethylene-polyoxypropylene-block polymers, methylcellulose, hydroxypropyl methylcellulose, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

"Pharmaceutically acceptable salts" refers to the relatively non-toxic, inorganic and organic acid addition salts, and base addition salts, of compounds of the present invention. The term "salt(s)", as employed herein, denotes acidic and/or basic salts formed with inorganic and/or organic acids and bases. Pharmaceutically acceptable (i.e., non-toxic, exhibiting minimal or no undesired toxicological effects, physiologically acceptable) salts are preferred. These salts can be prepared in situ during the final isolation and purification of the compounds, or at another stage of manufacturing. In particular, acid addition salts can be prepared by separately reacting the purified compound in its free base form with a suitable organic or inorganic acid and isolating the salt thus formed. Exemplary acid addition salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, sulfamates, malonates, salicylates, propionates, methylene-bis-β.-hydroxynaphthoates, gentisates, isethionates, di-p-toluoyltartrates, methanesulfonates, ethanesulfonates, benzenesulfonates, p-toluenesulfonates, cyclohexylsulfamates and laurylsulfonate salts, and the like. See, for example S. M. Berge, et al., "Pharmaceutical Salts," J. Pharm. Sci., 66, 1-19 (1977) which is incorporated herein by reference. Base addition salts can also be prepared by separately reacting the purified compound in its acid form with a suitable organic or inorganic base and isolating the salt thus formed. Base addition salts include pharmaceutically acceptable metal and amine salts. Suitable metal salts include the sodium, potassium, calcium, barium, zinc, magnesium, and aluminum salts. The sodium and potassium salts are preferred. Suitable inorganic base addition salts are prepared from metal bases which include sodium hydride, sodium hydroxide, potassium hydroxide, calcium hydroxide, aluminum hydroxide, lithium hydroxide, magnesium hydroxide, zinc hydroxide and the like. Suitable amine base addition salts are prepared from amines which have sufficient basicity to form a stable salt, and preferably include those amines which are frequently used in medicinal chemistry because of their low toxicity and acceptability for medical use. ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e.g., lysine and arginine, and dicyclohexylamine, and the like.

A sterol liposome entrapped agent may be administered in vivo by any suitable route including but not limited to: inoculation or injection (e.g. intravenous, intraperitoneal, intramuscular, subcutaneous, intra-aural, intraarticular, intramammary, and the like), topical application (e.g. on areas such as eyes, skin, in ears or on afflictions such as wounds and burns) and by absorption through epithelial or mucocutaneous linings (e.g., nasal, oral, vaginal, rectal, gastrointestinal mucosa, and the like). Other suitable means include but are not limited to: inhalation (e.g. as a mist or spray), orally (e.g. as a pill, capsule, liquid, etc.), intravaginally, intranasally, rectally, by ingestion of a food or probiotic product containing the antimicrobial peptide, as eye drops, incorporated into dressings or bandages (e.g. lyophilized forms may be included directly in the dressing), etc. In preferred embodiments, the mode of administration is topical or oral or by injection. In addition, the compositions may be administered in conjunction with other treatment modalities such as substances that boost the immune system, various chemotherapeutic agents (e.g. oxyurea), antibiotic agents, pain medication, with anti-anemia agents and/or in concert with blood transfusions, supplemental oxygen, treatment for various complications of hypoxia, and the like.

Administration of the compounds can be by any suitable route, including, without limitation, parenteral, oral, sublingual, transdermal, topical, intranasal, inhalation, intratracheal, or intrarectal. In some preferred embodiments, administration is orally, by injection, or by inhalation.

In some aspects, the disease that is treated is sickle cell disease (SCD), which may also be referred to as "sickle cell anemia". In other aspects, the disease that is treated is a hypoxia-underlying disease or condition. Allosteric effectors of Hb, including those that increase the oxygen affinity of hemoglobin, e.g. 5-HMF[9-14, 21-27] or those that decrease Hb affinity for oxygen, e.g. RSR13[28-33] are known to increase oxygenation to hypoxic tissues, potentially preventing cell death. The compounds described herein can also be used to increase tissue oxygenation. Some of the above literature compounds have also been investigated for stroke and myocardial ischemia; globally hyperfused states such as hemorrhage and sepsis; and as a means to hyperoxygenate tumors making them more susceptible to radiation therapy radiation therapy[28, 31, 33]. The compounds described herein can also be used to treat such conditions, and in some aspects, are used in combination with previously known compounds such as 5-HMF or RSR13.

The methods of the invention can be used to treat any patient or subject suffering from or likely to suffer from a disease or condition which can be prevented, treated, cured, or ameliorated (i.e. disease symptoms are abated) by increasing oxygenation to hypoxic tissues. Various embodiments or scenarios of use of the methods of the invention include but are not limited to patients who have incurred an acute or chronic illness or injury in which the body has become hypoxic. The agents act to enhance oxygen delivery from hemoglobin to the hypoxic tissue. Examples of such chronic or acute illnesses or injuries include but are not limited to hemorrhagic and traumatic shock, cardiac arrest and cardiogenic shock, traumatic brain injury, stroke, myocardial infarction, vaso-occlusive crisis, organ transplant, coronary heart disease, cerebrovascular disease, cancer, and others. These agents can also be used to hyperoxygenate tumors making them more susceptible to radiation therapy Before exemplary embodiments of the present invention are described in greater detail, it is to be understood that this invention is not limited to particular embodiments described, as such may, of course, vary. It is also to be understood that the terminology used herein is for the purpose of describing particular embodiments only, and is not intended to be limiting.

Where a range of values is provided, it is understood that each intervening value between the upper and lower limit of that range (to a tenth of the unit of the lower limit) is included in the range and encompassed within the invention, unless the context or description clearly dictates otherwise. In addition, smaller ranges between any two values in the range are encompassed, unless the context or description clearly indicates otherwise.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference, and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent", or "except for [a particular feature or element]", or "wherein [a particular feature or element] is not present (included, etc.) . . . ".

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

EXAMPLES

Example 1. Design and Synthesis of Azolylacryloyl Derivatives

Reagents and solvents for chemical synthesis were purchased from Sigma-Aldrich (USA) or Alfa Aeser (UK) or Acros Organics (Belgium) as ACS-reagent grade; and used without further purification. Anhydrous solvents were prepared according to standard methods.

Azolylacryloyl-carboxylate derivatives, e.g. KAUS-15 were previously designed to bind to βCys93 of Hb[20], the intention being to allosterically increase Hb affinity for oxygen and thus prevent polymerization of sickle Hb and red blood cell sickling[20]. However, when tested, these compounds showed very weak allosteric and/or antisickling properties, with some of the compounds even exhibiting a pro-sickling effect[20]. Structural studies of the compounds showed that they undergo a Michael addition reaction with the N-terminal Val1 amine in the α-cleft of Hb but not with βCys93 of Hb as anticipated[20]. The binding to the α-cleft of deoxygenated Hb led to stabilization of the T-state Hb due to the presence of the carboxylate moiety of the compounds, thus explaining their weak or opposite functional/biological activities[20].

Figure 1:
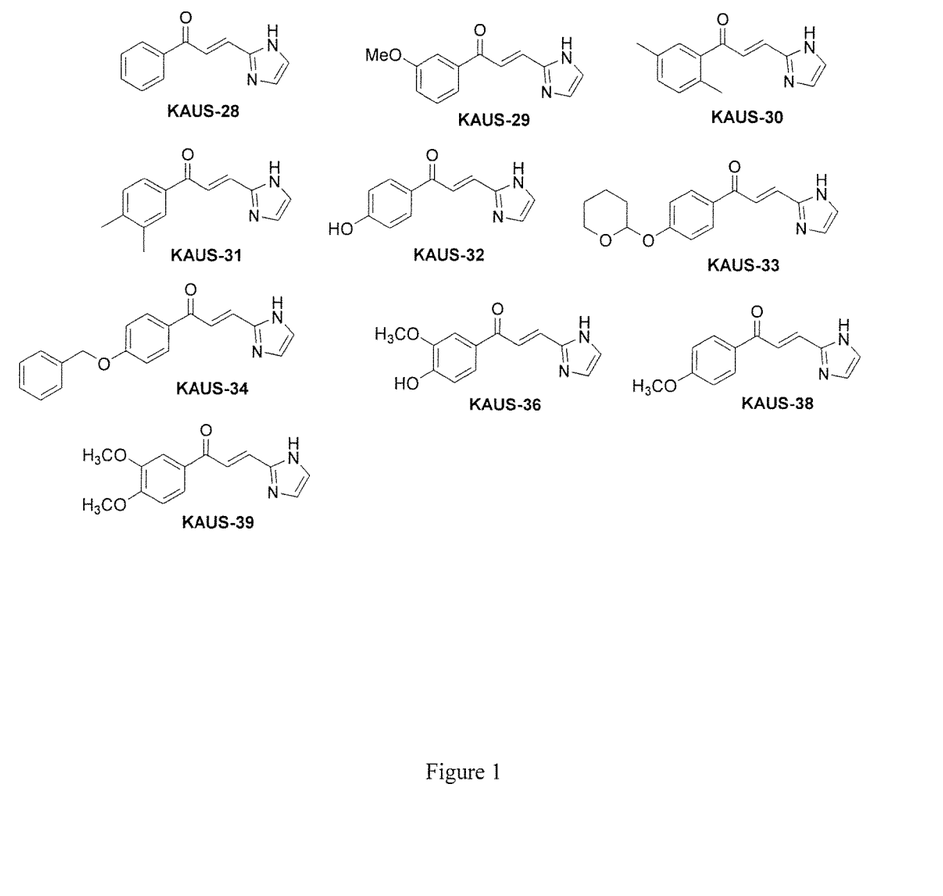
FIG. 1. Structures of exemplary azolylacryloyl derivatives.

In compounds described herein, the carboxylate moiety has been removed, thereby preventing interactions that stabilize the T-state Hb and leading to increased Hb oxygen affinity. The exemplary novel non-carboxylate azolylacryloyl derivatives include KAUS-28, KAUS-29, KAUS-30, KAUS-31, KAUS-32, KAUS-33, KAUS-34, KAUS-36, KAUS-38, and KAUS-39 (FIG. 1). These compounds are expected to undergo a Michael addition reaction with the βCys93 of Hb and/or with the N-terminal Val1 amine at the α-cleft. The former interactions would destabilize the T-state, while the latter is anticipated to stabilize the R-state, thereby shifting the OEC to the left and increasing the oxygen affinity of Hb. The above synthesized compounds have been evaluated in vitro for their binding interactions with free L-cysteine, and their allosteric and antisickling activities with hemoglobin.

Synthetic scheme 1 was followed for the synthesis of the above compounds. 2-imidazole carbaldehyde (2.88 g, 30 mmol) and substituted acetophenone (36 mmol) were dissolved in 40 ml of ethanol, and a 1N aqueous solution (40 ml) of sodium hydroxide was added to the solution. The mixture was stirred at room temperature for 8 hours. 1N hydrochloric acid (40 ml) was added to the resultant reaction mixture to conduct the extraction with chloroform. An organic layer was washed with saturated brine, dried and then concentrated under reduced pressure. The resultant residue was subjected to column chromatography on silica gel. Crystals obtained from a fraction eluted with 1% (v/v) methanol-chloroform were recrystallized from ethyl acetate.

Scheme 1

Ar = Phenyl,
3-methoxyphenyl
2,5-dimethylphenyl
3,4-dimethylphenyl
4-hydroxyphenyl 4-((tetrahydro-2H-pyran-2-yl)oxy)phenyl
4-(benzyloxy)phenyl
4-hydroxy-3-methoxyphenyl
4-methoxyphenyl
3,4-dimethoxyphenyl Synthesis of (E)-3-(1H-imidazol-2-yl)-1-phenyl-prop-2-en-1-one (KAUS-28)

1H-imidazole-2-carbaldehyde (2.88 g, 30 mmol) and acetophenone (4.32 g, 4.2 mL, 36 mmol) were dissolved in 40 ml of ethanol, and a 1N aqueous solution (40 ml) of sodium hydroxide was added to the solution. The mixture was stirred at room temperature for 8 hours. 1N Hydrochloric acid (40 ml) was added to the resultant reaction mixture to conduct the extraction with chloroform. An organic layer was washed with saturated brine, dried and then concentrated under reduced pressure. The resultant residue was subjected to column chromatography on silica gel. Crystals obtained from a fraction eluted with 1% (v/v) methanol-chloroform were recrystallized from ethyl acetate to obtain the titled compound as off-white powder (2.1 g, 60%). MP: 182-184° C. $^1$H NMR (850 MHz, DMSO-$d_6$) δ ppm 7.25-7.38 (m, 1H) 7.51 (d, J=15.57 Hz, 1H) 7.60 (t, J=7.79 Hz, 2H) 7.69 (t, J=7.27 Hz, 1H) 7.87 (d, J=15.57 Hz, 1H) 8.05 (d, J=7.27 Hz, 2H). $^{13}$C NMR (151 MHz, DMSO-$d_6$) δ 188.8, 143.4, 137.4, 133.2, 132.0, 128.9, 128.2, 121.1. HRMS (ESI) Calcd. m/z 199.0866; Found m/z 199.0850 (M+).

Synthesis of (E)-3-(1H-imidazol-2-yl)-1-(3-methoxyphenyl)prop-2-en-1-one (KAUS-29)

This compound was prepared following the procedure described above for the synthesis of the similar analogue KAUS-28 and was obtained as a yellowish solid (3.9 g, 57%). MP: 184° C. $^1$H NMR (850 MHz, DMSO-$d_6$) δ ppm 3.86 (s, 2H) 7.26 (dd, J=8.30, 2.59 Hz, 1H) 7.28-7.40 (m, 1H) 7.50 (d, J=15.57 Hz, 1H) 7.52-7.55 (m, 1H) 7.65 (d, J=7.78 Hz, 1H) 7.85 (d, J=15.57 Hz, 1H) 12.87 (br. s., 1H). $^{13}$C NMR (151 MHz, DMSO-$d_6$) δ 188.9, 160.1, 143.9, 139.4, 132.5, 130.6, 121.6, 121.2, 119.7, 113.2, 55.8. HRMS (ESI) Calcd. m/z 229.0972; Found m/z 229.0950 (M+).

Synthesis of (E)-1-(2,5-dimethylphenyl)-3-(1H-imidazol-2-yl)prop-2-en-1-one (KAUS-30)

This compound was prepared following the procedure described above for the synthesis of the similar analogue KAUS-28 and was obtained as an off-white solid (4.2 g, 62%). MP: 173-175° C. $^1$H NMR (850 MHz, DMSO-$d_6$) δ ppm 2.31 (s, 3H) 2.34 (s, 3H) 7.19 (d, J=16.09 Hz, 1H) 7.22-7.24 (m, 1H) 7.25-7.33 (m, 3H) 7.36 (s, 1H) 12.82 (br. s., 1H). $^{13}$C NMR (151 MHz, DMSO-$d_6$) δ 195.5, 143.5, 138.9, 135.3, 133.6, 131.7, 131.6, 128.9, 125.9, 20.9, 19.9. HRMS (ESI) Calcd. m/z 227.1179; Found m/z 227.1148 (M+).

Synthesis of (E)-1-(3,4-dimethylphenyl)-3-(1H-imidazol-2-yl)prop-2-en-1-one (KAUS-31)

This compound was prepared following the procedure described above for the synthesis of the similar analogue KAUS-28 and was obtained as a brownish solid (4.1 g, 61%). MP: 172-173° C. $^1$H NMR (850 MHz, DMSO-$d_6$) δ ppm 2.34 (s, 3H) 2.36 (s, 3H) 7.15-7.18 (m, 2H) 7.21 (d, J=16.09 Hz, 1H) 7.35 (d, J=16.09 Hz, 1H) 7.41 (br. s., 1H) 7.50-7.53 (m, 1H) 12.79 (br. s., 1H). $^{13}$C NMR (151 MHz, DMSO-$d_6$) δ 194.6, 143.6, 141.3, 137.3, 136.0, 133.1, 132.5, 129.0, 126.8, 125.8, 21.4, 20.6. HRMS (ESI) Calcd. m/z 227.1179; Found m/z 227.1143 (M+).

Preparation of 1-(4-((tetrahydro-2H-pyran-2-yl)oxy)phenyl)ethan-1-one

At room temperature and in an 80 mL dichloromethane solution, pyridinium p-toluenesulfonate (0.15 g, 0.6 mmol) and 4-hydroxyacetophenone (3.4 g, 25 mmol) were stirred for 0.5 h, after which and at the same temperature 3,4-dihydro-α-pyrane (11.77 g, 12.77 mL, 140 mmol), dissolved in 20 mL of dichloromethane and added dropwise. The reaction mixture was stirred at room temperature for 4 hrs and then washed twice with water, dried, and evaporated in vacuo. The yielded crude residue was recrystallized from petroleum ether to give a white solid of 1-(4-((tetrahydro-2H-pyran-2-yl)oxy)phenyl)ethan-1-one (yield 95%, m.p. 78-80° C.).

(E)-3-(1H-imidazol-2-yl)-1-(4-((tetrahydro-2H-pyran-2-yl)oxy)phenyl)prop-2-en-1-one (KAUS-33)

1H-imidazole-2-carbaldehyde and 1-(4-((tetrahydro-2H-pyran-2-yl)oxy)phenyl)ethan-1-one were reacted by the same procedure described above for the synthesis of KAUS-28 and was obtained as a whit solid (4.9 g, 51%). MP: 186-187° C. $^1$H NMR (850 MHz, DMSO-$d_6$) δ ppm 1.52-1.57 (m, 1H) 1.58-1.68 (m, 2H) 1.76-1.80 (m, 1H) 1.83-1.92

(m, 2H) 3.60 (dt, J=11.29, 4.22 Hz, 1H) 3.72-3.76 (m, 1H) 5.66 (t, J=3.37 Hz, 1H) 7.19-7.22 (m, 2H) 7.43 (br. s., 1H) 7.47 (d, J=15.57 Hz, 1H) 7.87 (d, J=15.57 Hz, 1H) 8.03-8.06 (m, 1H) 12.82 (br. s., 1H). $^{13}$C NMR (151 MHz, DMSO-$d_6$) δ 187.0, 160.5, 143.5, 131.3, 131.1, 130.9, 130.4, 130.0, 121.1, 119.9, 116.2, 115.5, 95.4, 61.7, 61.6, 29.5, 24.5, 18.3. HRMS (ESI) Calcd. m/z 299.1390; Found m/z 299.1337 (M+).

Synthesis of (E)-1-(4-hydroxyphenyl)-3-(1H-imidazol-2-yl)prop-2-en-1-one (KAUS-32)

KAUS-33 was stirred in 1N HCl at room temperature for 2 hrs after that, it was extracted using chloroform. An organic layer was washed with saturated brine, dried and then concentrated under reduced pressure. The resultant residue was subjected to column chromatography on silica gel. Crystals obtained from a fraction eluted with 1% (v/v) methanol-chloroform were recrystallized from ethyl acetate to obtain KAUS-32 as yellow crystals (3.1 g, 48%). MP: 250-253° C. $^1$H NMR (850 MHz, DMSO-$d_6$) δ ppm 6.88-6.97 (m, 2H) 7.15-7.29 (m, 1H) 7.35 (d, J=15.57 Hz, 1H) 7.45 (d, J=15.57 Hz, 1H) 7.87 (d, J'=15.57 Hz, 1H) 7.94-8.00 (m, 2H) 10.49 (br. s., 1H) 12.80 (br. s., 1H). $^{13}$C NMR (151 MHz, DMSO-$d_6$) δ 187.1, 162.8, 144.1, 131.5, 131.4, 129.4, 121.8, 116.0. HRMS (ESI) Calcd. m/z 215.0815; Found 215.0774 (M+).

Synthesis of (E)-1-(4-(benzyloxy)phenyl)-3-(1H-imidazol-2-yl)prop-2-en-1-one (KAUS-34)

In THF (100 mL) 4'-hydroxyacetophenone (0.05 mol), benzyl chlorides (0.065 mol), $K_2CO_3$ (10 g), and KI (0.3 g) were added. The mixture was stirred under reflux for 6 hrs. The solvent was removed in vacuo. Water (100 mL) was added and the mixture was extracted with $CHCl_3$, dried over MgSO4, and evaporated, the 4'-benzyloxyacetophenone was afforded as a white solid powder.
1H-imidazole-2-carbaldehyde and 4'-benzyloxyacetophenone were reacted as described above for the synthesis of the similar analogue KAUS-28 to afford KAUS-34 as off-white solid (4.8 g, 54%). MP: >250° C. decomposed. $^1$H NMR (850 MHz, DMSO-$d_6$) δ ppm 5.24 (s, 2H) 7.19 (d, J=8.30 Hz, 2H) 7.29 (s, 2H) 7.34-7.38 (m, 1H) 7.42 (t, J=7.53 Hz, 2H) 7.46-7.52 (m, 3H) 7.92-7.98 (m, 1H) 8.04-8.11 (m, 2H). $^{13}$C NMR (151 MHz, DMSO-$d_6$) δ 187.4, 162.8, 144.2, 136.9, 131.8, 131.1, 131.0, 129.0, 128.5, 128.4, 128.3, 128.2, 121.6, 115.4, 70.0 HRMS (ESI) Calcd. m/z 305.1285; Found m/z 305.1225 (M+).

Synthesis of (E)-1-(4-hydroxy-3-methoxyphenyl)-3-(1H-imidazol-2-yl)prop-2-en-1-one (KAUS-36)

This compound was prepared following the procedure described above for the synthesis of the similar analogue KAUS-28 and was obtained as a yellow solid (3 g, 42%). MP: >250° C. decomposed. $^1$H NMR (850 MHz, DMSO-$d_6$) δ ppm 3.89-3.93 (m, 2H) 6.99 (d, J=8.30 Hz, 1H) 7.50 (d, J=16.09 Hz, 1H) 7.70-7.73 (m, 1H) 7.77-7.81 (m, 1H) 7.86 (s, 1H). HRMS (ESI) Calcd. m/z 245.0921; Found m/z 245.0873 (M+).

Synthesis of (E)-3-(1H-imidazol-2-yl)-1-(4-methoxyphenyl)prop-2-en-1-one (KAUS-38)

This compound was prepared following the procedure described above for the synthesis of the similar analogue KAUS-28 and was obtained as a white solid (3.6 g, 53%). MP: 193-194° C. $^1$H NMR (850 MHz, DMSO-$d_6$) δ ppm 3.88 (s, 3H) 7.11-7.14 (m, 1H) 7.18 (br. s., 1H) 7.43 (br. s., 1H) 7.47 (d, J=15.57 Hz, 1H) 7.89 (d, J=15.57 Hz, 1H) 8.04-8.08 (m, 1H) 12.82 (br. s., 1H)

Synthesis of (E)-1-(3,4-dimethoxyphenyl)-3-(1H-imidazol-2-yl)prop-2-en-1-one (KAUS-39)

This compound was prepared following the procedure described above for the synthesis of the similar analogue KAUS-28 and was obtained as an off-white solid (2.7 g, 37%). MP: 222-223° C. $^1$H NMR (400 MHz, DMSO-$d_6$) δ ppm 3.88 (s, 3H) 3.90 (s, 3H) 7.16 (d, J=8.53 Hz, 1H) 7.20-7.34 (m, 1H) 7.37 (br. s., 1H) 7.50 (d, J=15.56 Hz, 1H) 7.58 (d, J=2.01 Hz, 1H) 7.78 (dd, J=8.53, 2.01 Hz, 1H) 7.90 (d, J=15.56 Hz, 1H).

Example 2. Reactivity of KAUS Compounds Toward Free Amino Acid, L-Cysteine

The above synthesized KAUS compounds were expected to covalently bind to Hb through a Michael addition reaction with the βCys93 at the surface of the protein to effect their allosteric and antisickling activities. We therefore investigated L-Cys conjugates with KAUS-28, KAUS-29, KAUS-33, KAUS-38 and KAUS-39 with ECA as a positive control using UPLC-MS analysis as previously described[20] with an Acquity H-Class UPLC which is connected to a PDA detector and an Acquity TQD detector. The column used was an Acquity UPLC BEH C18 1.7 μm, 2.1×50 mm, with a Vanguard pre-column attached. Solvent A consisted of water with 0.02% formic acid, while solvent B consisted of 90:10 acetonitrile:water with 0.02% formic acid. A gradient run was performed such that solvent B was increased from 0% B to 100% B from time 0-5 mins, followed by 3 minute wash at 100% B and then a return and re-equilibration at 100% A in the next 4 mins. The flow rate was maintained at 0.5 ml/min throughout the run. 2 μL of sample was injected per run. The eluent of the column was connected to a PDA UV detector which scanned from 220-350 nm and showed a 2D channel of 280 nm. The eluent was then introduced into the TQD detector. The TQD detector was set at positive ionization mode with a capillary voltage of 3.20 kV, cone voltage of 20 V, extractor voltage of 1 V, and RF lens voltage of 0.1 V. The source temperature was set at 150° C., while the desolvation temperature was set at 350° C. and the desolvation and cone gas flows were set at 650 and 50 L/hr respectively. Scans were made from 100-700 m/z with scan duration of 0.5 seconds to obtain mass spectra at different time points.

The UPLC-MS analysis of the reaction between the compounds and L-Cys and (that was incubated for 3 hours) is shown in Table 1. KAUS-38 was the most reactive (37.8%), followed by KAUS-39 (27.2%) and KAUS-333 (24.8), while KAUS-28 and KAUS 29 showed the least reactivity (<10%). This study clearly suggest the compounds are capable of interacting with the free thiol of βCys93 of Hb.

TABLE 1

UPLC-MS Measurements of Relative Ratio of Azolylacryloyl Compounds and their Adduct Products with L-Cysteine

| Compound | Peak | RT[a] (min) | Max. m/z | Area | Ratio of Cpd/Adduct |
|---|---|---|---|---|---|
| Ethacrynic Acid | Compound | 4.43 | 302.7 | 898 | 3.7 |
| | Adduct | 2.63 | 423.7 | 23733 | 96.3 |
| KAUS-28 | Compound | 1.9 | 199.1 | 9720.5 | 93.1 |
| | Adduct | 1.5 | 320.2 | 725.5 | 6.9 |
| KAUS-29 | Compound | 1.9 | 229.1 | 12530 | 97.9 |
| | Adduct | 1.5 | 350.2 | 264.5 | 2.1 |
| KAUS-33[b] | Compound | 1.7 | 215.1 | 9235 | 75.2 |
| | Adduct | 1.2 | 336.2 | 3048.5 | 24.8 |
| KAUS-38 | Compound | 2.1 | 229.1 | 6219 | 62.2 |
| | Adduct | 1.7 | 350.2 | 3776.5 | 37.8 |
| KAUS-39 | Compound | 2.0 | 259.2 | 6279 | 72.8 |
| | Adduct | 1.6 | 380.2 | 2344.5 | 27.2 |

[a]RT = Retention Time.
[b]Loss of THP ether due to phosphoric acid treatment

Example 3. Oxygen Equilibrium Curve (OEC) Studies

De-identified, leftover EDTA venous blood samples from patients with SCD who visited The Children's Hospital of Philadelphia for routine clinic visits, were obtained after informed consent and used for antisickling study. Normal whole blood was collected from adult donors at the Virginia Commonwealth University after informed consent and used for oxygen equilibrium curve study. Hb was purified from discarded normal blood samples following published procedure and used for OEC study[34]. The use of these human samples is in accordance with regulations of the IRB for Protection of Human Subjects.

The ability of the KAUS compounds to left-shift the OEC (stabilize the R-state and/or destabilize the T-state) and increase the oxygen affinity of Hb in normal whole blood or free human hemoglobin was determined by multipoint tonometry as previously reported[20]. First, cell free normal human hemoglobin (1 mM) or normal whole blood (hematocrit of 20%) was incubated with 1 mM or 2 mM final test compound (KAUS-28, KAUS-29, KAUS-33, KAUS-38 or KAUS-39) for 1.5 h at 37° C. Following incubation, the mixture was equilibrated in a tonometer with oxygen tensions of 6, 20 and 60 mmHg for 10 min each, and $pO_2$ (mmHg) and $sO_2$ (%) values were measured thereafter using ABL 700 series automated blood gas analyzer (Radiometer America, Inc., Westlake, Ohio). The measured values of $pO_2$ and $sO_2$ at each oxygen tension level were then subjected to a non-linear regression analysis using the program Scientist (Micromath, Salt Lake City, Utah) to calculate $P_{50}$ and the Hill coefficient (N) values. Time-dependent OEC studies (1 hr, 4 hr, 8 hr and 12 hr) were also performed for KAUS-28, KAUS-33, KAUS-38, and KAUS-39 at final compound concentration of 2 mM. ECA and the previously studied azolylacryloyl-carboxylate derivative, KAUS-15 were used as positive controls. Compounds were dissolved in DMSO to make 100-250 mM stock solutions, and DMSO was used in all control samples. All OEC studies were performed in duplicates.

Figure 2:
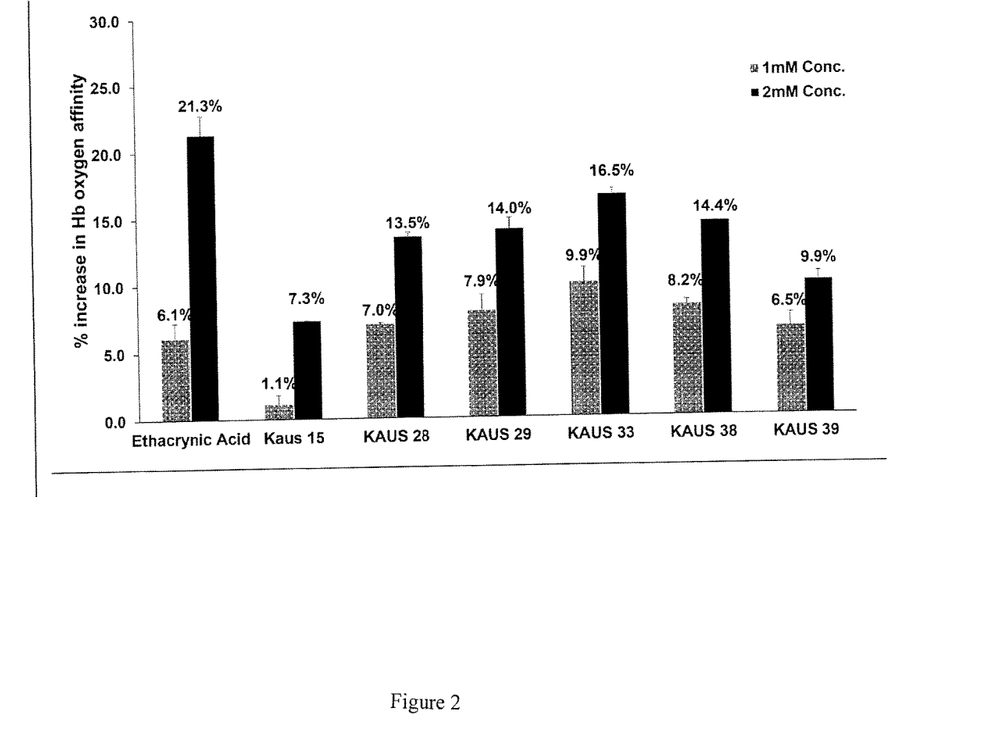
FIG. 2. Effect of KAUS compounds on Hb affinity for oxygen in normal whole blood.
Figure 3:
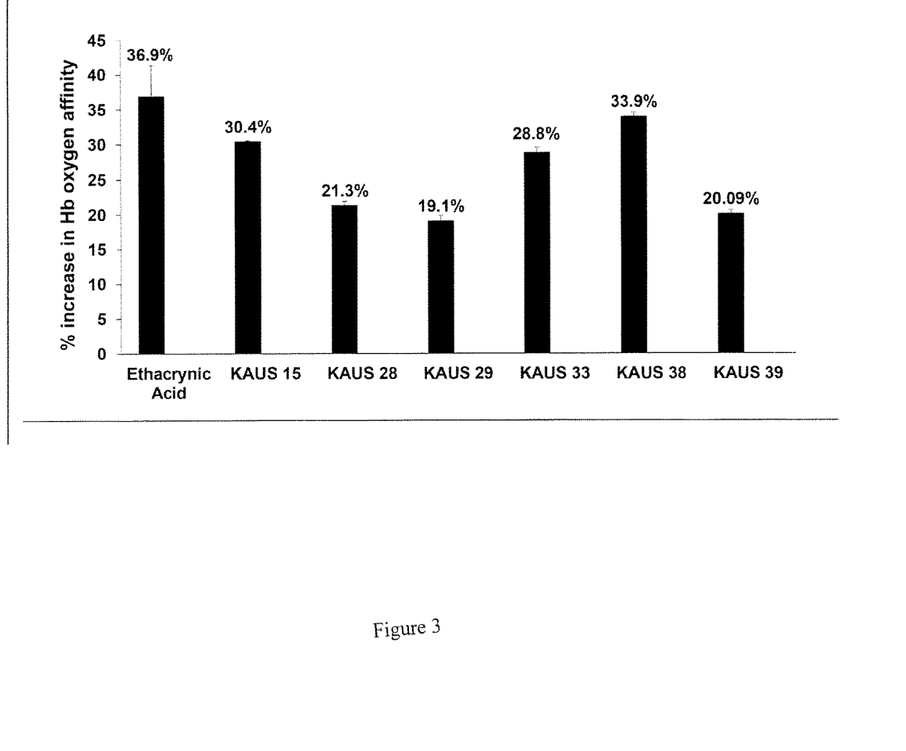
FIG. 3. Effect of 2 mM KAUS compounds on Hb affinity for oxygen in cell free hemoglobin.
Figure 4:
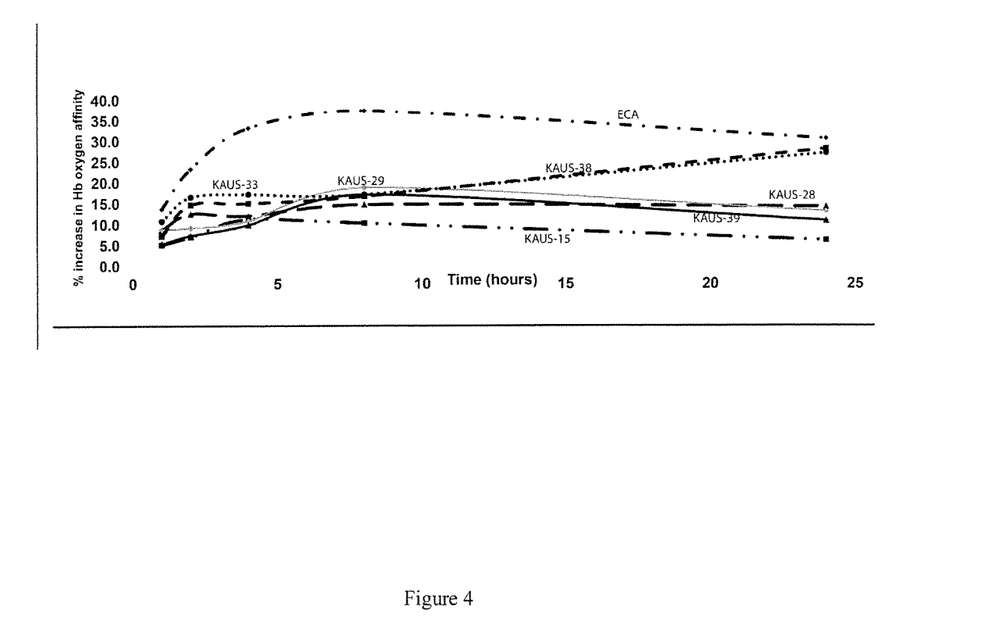
FIG. 4. Time dependent effect of 2 mM KAUS compounds on Hb affinity for oxygen in human blood.
Figure 5:
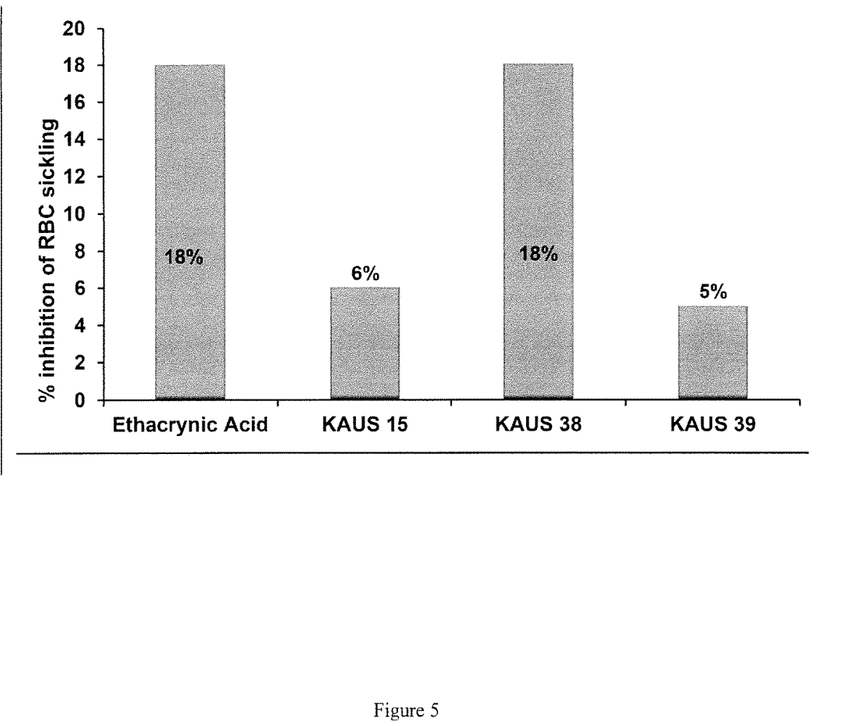
FIG. 5. Effect of KAUS compounds on sickle red blood cell morphology.

The OEC results with whole blood and cell free hemoglobin are shown in FIGS. 2 and 3. All compounds increased Hb affinity for oxygen whether tested with cell free Hb or whole blood. Nonetheless, the compounds showed significantly more potent effect with cell free Hb than with whole blood, especially with the control KAUS-15, suggesting that serum (plasma) proteins and/or the RBC membrane may be having negative effect on the compounds ability to bind to hemoglobin. The compounds also showed concentration-dependent OEC effect. In whole blood KAUS-33 showed the most potent effect (9.9 and 16.5% at 1 mM and 2 mM, respectively), followed by KAUS-38 and KAUS-29 (8 and 14%, at 1 mM and 2 mM, respectively). These values compare with the positive control, ECA at 6.1 and 21.3%, and KAUS-15 at 1 and 7%, respectively. The results clearly suggest improvement in the allosteric properties of these new compounds when compared with KAUS-15 that contains a carboxylate moiety. The ability to increase the oxygen affinity of Hb makes these compounds potential antisickling agents. The time-dependent studies showed that at 2 mM concentration, all of the compounds sustained their activity throughout the 24 hour experiment (FIG. 4). This observation contrasts with most aromatic aldehyde antisickling agents which suffer from rapid metabolism and thus have short pharmacologic activities[9, 13]. Thus, as proposed the azolylacryloyl derivatives appears to have superior in vitro allosteric effect than the carboxylate-containing azolylacryloyl, as well as metabolically stable than some of the previously studied antisickling aromatic aldehydes.

Example 4. RBC Morphological Antisickling Studies

Compounds that increase the oxygen affinity of Hb are expected to inhibit RBC sickling as high-$O_2$-affinity sickle Hb does not polymerize[9, 13]. KAUS-38 and KAUS-39 at 2 mM concentrations were tested for their abilities to prevent RBC sickling under hypoxic condition following previously reported assay[20]. Briefly SS cells were suspended in Hemox buffer (TCS Scientific Corp, Southampton, Pa.), pH 7.4, that contained 10 mM glucose and 0.2% bovine serum albumin. The solution was incubated under air in the absence (control) or presence of two 2 mM concentration of test compound at 37° C. for 1 hr. Following, the suspension was incubated under hypoxic condition (4% oxygen/96% nitrogen) at 37° C. for 5 hrs. The suspension was fixed with 2% glutaraldehyde solution without exposure to air and then subjected to microscopic morphological analysis as previously reported polymerize[20]

As expected from their ability to increase the oxygen affinity of Hb, the two compounds KAUS-38 and KAUS-39 were able to reduce sickling by 18% and 5%, respectively at 2 mM. This compares with the positive controls ECA that inhibited 18% RBC sickling, while KAUS-15 inhibited 6% sickling.

In conclusion, the structural modification of the carboxylate-containing azolylacryloyl into novel non-carboxylate compounds has led to improvement in the allosteric properties of these compounds, as well as enhanced the biological activity of a tested compound.

While the invention has been described in terms of its several exemplary embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

REFERENCES

1. Habara, A.; Steinberg, M. H. Minireview: Genetic basis of heterogeneity and severity in sickle cell disease. *Exp. Biol. Med.* (*Maywood*) 2016, 241, 689-696.

2. Akinsheye, I.; Klings, E. S. Sickle cell anemia and vascular dysfunction: the nitric oxide connection. *J. Cell. Physiol.* 2010, 224, 620-625.
3. De Franceschi, L. Pathophisiology of sickle cell disease and new drugs for the treatment. *Mediterr. J. Hematol. Infect. Dis.* 2009, 1, e2009024.
4. Turhan, A.; Weiss, L. A.; Mohandas, N.; Coller, B. S.; Frenette, P. S. Primary role for adherent leukocytes in sickle cell vascular occlusion: a new paradigm. *Proc. Natl. Acad. Sci. U.S.A.* 2002, 99, 3047-3051.
5. Platt, O. S. Hydroxyurea for the treatment of sickle cell anemia. *N Engl. J. Med.* 2008, 358, 1362-1369.
6. Jensen, F. B. The dual roles of red blood cells in tissue oxygen delivery: oxygen carriers and regulators of local blood flow. *J. Exp. Biol.* 2009, 212, 3387-3393.
7. Rogers, S. C.; Ross, J. G.; d'Avignon, A.; Gibbons, L. B.; Gazit, V.; Hassan, M. N.; McLaughlin, D.; Griffin, S.; Neumayr, T.; Debaun, M.; DeBaun, M. R.; Doctor, A. Sickle hemoglobin disturbs normal coupling among erythrocyte O2 content, glycolysis, and antioxidant capacity. *Blood* 2013, 121, 1651-1662.
8. Zhang, Y.; Berka, V.; Song, A.; Sun, K.; Wang, W.; Zhang, W.; Ning, C.; Li, C.; Zhang, Q.; Bogdanov, M.; Alexander, D. C.; Milburn, M. V.; Ahmed, M. H.; Lin, H.; Idowu, M.; Zhang, J.; Kato, G. J.; Abdulmalik, O. Y.; Zhang, W.; Dowhan, W.; Kellems, R. E.; Zhang, P.; Jin, J.; Safo, M.; Tsai, A. L.; Juneja, H. S.; Xia, Y. Elevated sphingosine-1-phosphate promotes sickling and sickle cell disease progression. *J. Clin. Invest.* 2014, 124, 2750-2761.
9. Safo, M. K.; Kato, G. J. Therapeutic strategies to alter the oxygen affinity of sickle hemoglobin. *Hematol. Oncol. Clin. North Am.* 2014, 28, 217-231.
10. Safo, M. K.; Ahmed, M. H.; Ghatge, M. S.; Boyiri, T. Hemoglobin-ligand binding: Understanding Hb function and allostery on atomic level. *Biochim. Biophys. Acta* 2011, 1814, 797-809.
11. Safo, M. K.; Bruno, S. Allosteric Effectors of Hemoglobin: Past, Present and Future. In *Chemistry and Biochemistry of Oxygen Therapeutics: From Transfusion to Artificial Blood*; Mozzarelli, A., and Bettati, S., Eds.; John Wiley & Sons, Ltd: 2011; pp 285-300.
12. Abdulmalik, O.; Ghatge, M. S.; Musayev, F. N.; Parikh, A.; Chen, Q.; Yang, J.; Nnamani, I. N.; Danso-Danquah, R.; Eseonu, D. N.; Asakura, K.; Abraham, D. J.; Venitz, J.; Safo, M. K. Crystallographic analysis of human hemoglobin elucidates the structural basis of the potent and dual antisickling activity of pyridyl derivatives of vanillin. 2011, D67, 920-928.
13. Abdulmalik, O.; Safo, M. K.; Chen, Q.; Yang, J.; Brugnara, C.; Ohene-Frempong, K.; Abraham, D. J.; Asakura, T. 5-Hydroxymethyl-2-Furfural Modifies Intracellular Sickle Haemoglobin and Inhibits Sickling of Red Blood Cells. *Br. J. Haematol.* 2005, 128, 552-561.
14. Safo, M. K.; Abdulmalik, O.; Danso-Danquah, R.; Burnett, J. C.; Nokuri, S.; Joshi, G. S.; Musayev, F. N.; Asakura, T.; Abraham, D. J. Structural basis for the potent antisickling effect of a novel class of five-membered heterocyclic aldehydic compounds. *J. Med. Chem.* 2004, 47, 4665-4676.
15. Arya, R.; Rolan, P. E.; Wootton, R.; Posner, J.; Bellingham, A. J. Tucaresol increases oxygen affinity and reduces haemolysis in subjects with sickle cell anaemia. *Br. J. Haematol.* 1996, 93, 817-821.
16. Oksenberg, D.; Dufu, K.; Patel, M. P.; Chuang, C.; Li, Z.; Xu, Q.; Silva-Garcia, A.; Zhou, C.; Hutchaleelaha, A.; Patskovska, L.; Patskovsky, Y.; Almo, S. C.; Sinha, U.; Metcalf, B. W.; Archer, D. R. GBT440 increases hemoglobin oxygen affinity, reduces sickling and prolongs RBC half-life in a murine model of sickle cell disease. *Br. J. Haematol.* 2016.
17. Zaugg, R. H.; Walder, J. A.; Klotz, I. M. Schiff base adducts of hemoglobin. Modifications that inhibit erythrocyte sickling. *J. Biol. Chem.* 1977, 252, 8542-8548.
18. Kennedy, P. E.; Williams, F. L.; Abraham, D. J. Design, synthesis, and testing of potential antisickling agents. 3. Ethacrynic acid. *J. Med. Chem.* 1984, 27, 103-105.
19. Perutz, M. F.; Fermi, G.; Abraham, D. J.; Poyart, C.; Bursaux, E. Hemoglobin as a receptor of drugs and peptides: x-ray studies of the stereochemistry of binding. *J. Am. Chem. Soc.* 1986, 108, 1064-1078.
20. Omar, A. M.; Mahran, M. A.; Ghatge, M. S.; Chowdhury, N.; Bamane, F. H.; El-Araby, M. E.; Abdulmalik, O.; Safo, M. K. Identification of a novel class of covalent modifiers of hemoglobin as potential antisickling agents. *Org. Biomol. Chem.* 2015.
21. Li, M. M.; Wu, L. Y.; Zhao, T.; Wu, K. W.; Xiong, L.; Zhu, L. L.; Fan, M. The protective role of 5-hydroxymethyl-2-furfural (5-HMF) against acute hypobaric hypoxia. *Cell Stress Chaperones* 2011, 16, 529-537.
22. Li, M. M.; Wu, L. Y.; Zhao, T.; Xiong, L.; Huang, X.; Liu, Z. H.; Fan, X. L.; Xiao, C. R.; Gao, Y.; Ma, Y. B.; Chen, J. J.; Zhu, L. L.; Fan, M. The protective role of 5-HMF against hypoxic injury. *Cell Stress Chaperones* 2011, 16, 267-273.
23. Mariacher, C.; Gatterer, H.; Greilberger, J.; Djukic, R.; Greilberger, M.; Philippe, M.; Burtscher, M. Effects of Antioxidant Supplementation on Exercise Performance in Acute Normobaric Hypoxia. *Int. J. Sport Nutr. Exerc. Metab.* 2013.
24. Gu, H.; Jiang, Y. B.; Jiang, H. Y.; Xu, D. Q.; Yu, J. T.; Ding, X.; Zhao, F. M.; Zhan, Z.; Wang, M. Y. Effect of 5-hydroxymethyl furfural on BCL-2 and NF-kappaB gene expression of apoptotic rat hippocampal neurons injured by H2O2. *Zhong Yao Cai* 2011, 34, 1753-1756.
25. Zhao, L.; Chen, J.; Su, J.; Li, L.; Hu, S.; Li, B.; Zhang, X.; Xu, Z.; Chen, T. In vitro antioxidant and antiproliferative activities of 5-hydroxymethylfurfural. *J. Agric. Food Chem.* 2013, 61, 10604-10611.
26. Wang, M. Y.; Zhao, F. M.; Peng, H. Y.; Lou, C. H.; Li, Y.; Ding, X.; Yu, X. Y.; Yang, G. M.; Xu, D. Q.; Jiang, L. H.; Zhang, X.; Ye, L. H.; Cai, B. C. Investigation on the morphological protective effect of 5-hydroxymethylfurfural extracted from wine-processed Fructus corni on human L02 hepatocytes. *J. Ethnopharmacol.* 2010, 130, 424-428.
27. He, Y. L.; Li, M. M.; Wu, L. Y.; Zhao, T.; Di, Y.; Huang, X.; Ding, X. F.; Wu, K. W.; Fan, M.; Zhu, L. L. Enhanced hypoxia-inducible factor (HIF)-1alpha stability induced by 5-hydroxymethyl-2-furfural (5-HMF) contributes to protection against hypoxia. *Mol. Med.* 2015, 20, 590-600.
28. Scott, C.; Suh, J.; Stea, B.; Nabid, A.; Hackman, J. Improved survival, quality of life, and quality-adjusted survival in breast cancer patients treated with efaproxiral (Efaproxyn) plus whole-brain radiation therapy for brain metastases. *Am. J. Clin. Oncol.* 2007, 30, 580-587.
29. Kunert, M. P.; Liard, J. F.; Abraham, D. J. RSR-13, an allosteric effector of hemoglobin, increases systemic and iliac vascular resistance in rats. *Am. J. Physiol.* 1996, 271, H602-13.
30. Abraham, D. J.; Wireko, F. C.; Randad, R. S.; Poyart, C.; Kister, J.; Bohn, B.; Liard, J. F.; Kunert, M. P. Allosteric modifiers of hemoglobin: 2-[4-[[(3,5-disubstituted anilino)carbonyl]methyl]phenoxy]-2-methylpropionic acid derivatives that lower the oxygen affinity of hemoglobin in red cell suspensions, in whole blood, and in vivo in rats. *Biochemistry* 1992, 31, 9141-9149.

31. Grinberg, O. Y.; Miyake, M.; Hou, H.; Steffen, R. P.; Swartz, H. M. The dose-dependent effect of RSR13, a synthetic allosteric modifier of hemoglobin, on physiological parameters and brain tissue oxygenation in rats. *Adv. Exp. Med. Biol.* 2003, 530, 287-296.

32. Pagel, P. S.; Hettrick, D. A.; Montgomery, M. W.; Kersten, J. R.; Warltier, D. C. RSR13, a synthetic allosteric modifier of hemoglobin, enhances recovery of stunned myocardium in dogs. *Adv. Exp. Med. Biol.* 1998, 454, 527-531.

33. Miyake, M.; Grinberg, O. Y.; Hou, H.; Steffen, R. P.; Elkadi, H.; Swartz, H. M. The effect of RSR13, a synthetic allosteric modifier of hemoglobin, on brain tissue pO2 (measured by EPR oximetry) following severe hemorrhagic shock in rats. *Adv. Exp. Med Biol.* 2003, 530, 319-329.

34. Safo, M. K.; Abraham, D. J. X-ray crystallography of hemoglobins. Methods *Mol. Med.* 2003, 82, 1-19.

We claim:

1. A method of treating sickle cell disease in a subject in need thereof, comprising
administering to the subject a therapeutically effective amount of a compound of Formula I

Formula I where V is selected from the group consisting of O, S, and NH, where W is selected from the group consisting of N and CH, and where $R_1$, $R_2$, $R_3$, $R_4$, $R_5$ and $R_6$ are the same or different and are independently any of i) H, OH, or halogen, ii) substituted or unsubstituted alkyl, alkoxy, hydroxyl-alkyl, halogen, aryl or O-aryl; or iii) M, where M is where
$R_7$ and $R_8$ are the same or different and are independently H, OH, alkyl, alkoxy, hydroxyl-alkyl, halogen, aryl or O-aryl;
X, Y and Z may be the same or different and are independently C or N; and
B is a bridging moiety that connects M to the phenyl moiety of Formula I.

2. A method of treating a hypoxia-associated disease or condition in a subject in need thereof, comprising
administering to the subject a therapeutically effective amount of a compound of Formula I Formula I where V is selected from the group consisting of O, S, and NH, where W is selected from the group consisting of N and CH, and where $R_1$, $R_2$, $R_3$, $R_4$, $R_5$ and $R_6$ are the same or different and are independently any of i) H, OH, or halogen, ii) substituted or unsubstituted alkyl, alkoxy, hydroxyl-alkyl, halogen, aryl or O-aryl; or iii) M, where M is where
$R_7$ and $R_8$ are the same or different and are independently H, OH, alkyl, alkoxy, hydroxyl-alkyl, halogen, aryl or O-aryl;
X, Y and Z may be the same or different and are independently C or N; and
B is a bridging moiety that connects M to the phenyl moiety of Formula I, wherein the hypoxia-associated disease or condition is selected from the group consisting of hemorrhagic shock, traumatic shock, cardiac arrest, cardiogenic shock, traumatic brain injury, stroke, myocardial infarction, myocardial ischemia, and vaso-occlusive crisis.

* * * * *